(12) United States Patent
Wulf et al.

(10) Patent No.: US 10,716,855 B2
(45) Date of Patent: Jul. 21, 2020

(54) PULSE PHOTODYNAMIC TREATMENT OF PHOTODAMAGED SKIN

(71) Applicant: GALDERMA RESEARCH & DEVELOPMENT, Biot (FR)

(72) Inventors: Hans Christian Wulf, Espergaerde (DK); Gloria Sanclemente, Medellin (CO)

(73) Assignee: GALDERMA RESEARCH & DEVELOPMENT, Biot (FR)

( * ) Notice: Subject to any disclaimer, the term of this patent is extended or adjusted under 35 U.S.C. 154(b) by 0 days.

(21) Appl. No.: 15/103,603

(22) PCT Filed: Dec. 5, 2014

(86) PCT No.: PCT/EP2014/076796
§ 371 (c)(1),
(2) Date: Jun. 10, 2016

(87) PCT Pub. No.: WO2015/091037
PCT Pub. Date: Jun. 25, 2015

(65) Prior Publication Data
US 2016/0287701 A1 Oct. 6, 2016

(30) Foreign Application Priority Data

Dec. 20, 2013 (EP) .................................... 13306826
Mar. 28, 2014 (EP) .................................... 14162516

(51) Int. Cl.
| A61K 41/00 | (2020.01) |
| A61K 31/197 | (2006.01) |
| A61K 31/22 | (2006.01) |
| A61N 5/06 | (2006.01) |
| A61M 37/00 | (2006.01) |

(52) U.S. Cl.
CPC ........ *A61K 41/0061* (2013.01); *A61K 31/197* (2013.01); *A61K 31/22* (2013.01); *A61M 37/00* (2013.01); *A61M 37/0015* (2013.01); *A61N 5/062* (2013.01); *A61M 2037/0007* (2013.01); *A61M 2037/0023* (2013.01); *A61M 2037/0061* (2013.01); *A61N 2005/0652* (2013.01); *A61N 2005/0653* (2013.01); *A61N 2005/0657* (2013.01); *A61N 2005/0663* (2013.01)

(58) Field of Classification Search
CPC .................................................. A61K 41/0061
See application file for complete search history.

(56) References Cited

U.S. PATENT DOCUMENTS

| 5,079,262 A | 1/1992 | Kennedy et al. |
| 5,211,938 A | 5/1993 | Kennedy et al. |
| 5,234,940 A | 8/1993 | Kennedy et al. |
| 5,422,093 A | 6/1995 | Kennedy et al. |
| 6,034,267 A | 3/2000 | Gierskcky et al. |
| 9,249,086 B2* | 2/2016 | Brænden ............ A61K 41/0061 |
| 2010/0137439 A1* | 6/2010 | Wulf .................... A61K 31/221 514/561 |
| 2010/0211137 A1 | 8/2010 | Kim et al. |
| 2010/0255079 A1 | 10/2010 | Sanmiguel et al. |
| 2010/0305495 A1 | 12/2010 | Anderson et al. |
| 2014/0067024 A1* | 3/2014 | Jones ..................... A61N 5/062 607/90 |

FOREIGN PATENT DOCUMENTS

| JP | 2008-519812 | 6/2008 |
| JP | 2010-515714 | 5/2010 |
| WO | 91/01727 A2 | 2/1991 |
| WO | 96/28412 A1 | 9/1996 |
| WO | 02/10120 A1 | 2/2002 |
| WO | WO-02/13788 A1 | 2/2002 |
| WO | 2005/092838 A1 | 10/2005 |
| WO | 2006/051269 A1 | 5/2006 |
| WO | WO-2008/084241 A2 | 7/2008 |

OTHER PUBLICATIONS

Dermoabrasion Definition, Medline Dictionary, http://medical-dictionary.thefreedictionary.com/dermoabrasion, accessed Oct. 16, 2017, 1 page. (Year: 2017).*
Bissonnette et al. (Short Incubation photodynamic therapy with methylaminolevulinate and no occlusion for the treatment of actinic keratosis, 2012, J. Am. Acad. Dermatol., vol. 67(6), pp. 1386-1387. (Year: 2012).*
Wiegell et al. "Continuous activation of PpIX by daylight is as effective and less painful than conventional photodynamic therapy . . . ", British Journal of Dermatology, 2008, vol. 158, pp. 740-746.*
Wiegell et al., British Journal of Dermatology, 2012, 166(6): 1327-1332.*
Gilbert, D.J., "Incorporating Photodynamic Therapy into a Medical and Cosmetic Dermatology Practice," Dermatologic Clinics, W.B. Sunders Co., London, GB, vol. 25, No. 1, Jan. 2007, pp. 111-118.
Togsverd-Bo, K., et al., "Intensified photodynamic therapy of actinic keratoses with fractional CO2 laser: a randomized clinical trial," British Journal of Dermatology, vol. 166, No. 6, May 2012, pp. 1262-1269.
Baumann, L, "Skin ageing and its treatment," J Pathol., 2007, 211(2), pp. 241-251.
Han, A., et al., "Photoaging.," Dermatol Clin. 2014, pp. 291-299 (Abstract only).
Shamban, AT, "Current and new treatments of photodamaged skin" Facial Plast Surg, Dec. 2009, 25(5), pp. 337-346 (Abstract only).
Chronic actinic damage of facial skin. Clin Dermatol. Nov.-Dec. 2014;32(6):752-62 (Abstract only).
Kennedy, J.C. et al., "Photodynamic therapy (PDT) and photodiagnosis (PD) using endogenous photosensitization induced by 5-aminolevulinic acid )ALA); mechanisms and clinical results," J. Clin Laser Med Surg., Oct. 1996, 14, pp. 289-304 (Abstract only).

(Continued)

*Primary Examiner* — Rei Tsang Shiao
(74) *Attorney, Agent, or Firm* — Foley & Lardner LLP; S. Talapatra

(57) ABSTRACT

A pulse photodynamic therapy (or pulse PDT) treatment of photodamaged skin is described.

11 Claims, 12 Drawing Sheets

(56) References Cited

OTHER PUBLICATIONS

S. R. Wiegell et al., "A randomized, multicentre study of directed daylight exposure times of 1 1/2 vs. 2 1/2 h in daylight-mediated photodynamic therapy with methyl aminolaevulinate in patients with multiple thin actinic keratoses of the face and scalp," British Journal of Dermatology, vol. 164, No. 5, Apr. 5, 2011, pp. 1083-1090, XP055472249, ISSN: 0007-0963, DOI: 10.1111/j.1365-2133.2011.10209.x.

De Leeuw, J., et al., "Photodynamic therapy of acne vulgaris using 5-aminolevulinic acid 0.5% liposomal spray and Intense pulsed light in combination with topical keratolytic agents," Journal of the European Academy of Dermatology and Venereology, vol. 2, No. 4, Apr. 2010, pp. 460-469.

Hovenic, W. et al., "#R23 Daylight Photodynamic Therapy (D-PDT) for Severe Inflammatory Acne", www_aslms.org, Apr. 6, 2014, Retrieved from the Internet: URL:http://www.aslms.org/annualconference.resident_fellow_abstracts.shtml [retrieved on Feb. 11, 2015] abstract, 2 pages.

International Preliminary Report on Patentability dated Jun. 30, 2016 corresponding to International Patent Application No. PCT/EP2014/076796, 9 pages.

International Preliminary Report on Patentability dated Jun. 30, 2016 corresponding to International Patent Application No. PCT/EP2014/078931, 10 pages.

International Search Report and Written Opinion dated Mar. 4, 2015 corresponding to International Patent Application No. PCT/EP2014/078931, 12 pages.

Nestor, M.S., et al., "The Use of Photodynamic Therapy in Dermatology: Results of a Consensus Conference," Journal Drugs in Dermatology, vol. 5, No. 2, Feb. 2006, pp. 140-154.

Wiegell, S.R., et al., "Photodynamic therapy of acne vulgaris using methyl aminolaevulinate: a blinded, randomized, controlled trial," British Journal of Dermatology, vol. 154, No. 5, May 2006, pp. 969-976.

International Search Report and Written Opinion dated Feb. 19, 2015 corresponding to International Patent Application No. PCT/EP2014/076796, 12 pages.

Clementoni, M. T., et al., "Photodynamic Photorejuvenation of the Face With a Combination of Microneedling, Red Light, and Broadband Pulsed Light," Lasers in Surgery and Medicine, vol. 42, No. 2, Feb. 2010, pp. 150-159.

Torezan, L., et al., "A Pilot Split-Face Comparing Conventional Methyl Aminolevulinate-Photodynamic Therapy (PDT) With Microneedling-Assisted PDT on Actinically Damaged Skin," Dermatologic Surgery, vol. 39, No. 8, Aug. 2013, pp. 1197-1201.

\* cited by examiner

PULSE PHOTODYNAMIC TREATMENT OF PHOTODAMAGED SKIN

CROSS-REFERENCE TO PRIOR APPLICATIONS

This application is a National Stage of PCT/EP2014/076796, filed Dec. 5, 2014, and designating the United States (published on Jun. 25, 2015, as WO 2015/091037 A1), which claims priority under 35 U.S.C. § 119 to European Patent Application No. 14162516.0, filed Mar. 28, 2014, and European Patent Application No. 13306826.2, filed Dec. 20, 2013, each hereby expressly incorporated by reference in its entirety and each assigned to the assignee hereof.

FIELD OF THE INVENTION

The present invention is related to a pulse photodynamic therapy (or pulse PDT) treatment of photodamaged skin.

BACKGROUND OF THE INVENTION

Photodamaged or sun damaged skin occurs with exposure to sunlight (UVA or UVB). Twenty five percent of our lifetime exposure occurs before the end of our teenage years. Photodamage is considered to be the structural and functional deterioration of chronically sun-exposed skin. Keratinocytes, melanocytes, fibroblasts and endothelial cells are altered by UV radiation resulting in changes in skin texture, altered skin tightness and thickness, sallowness, dyschromia, wrinkles, telangiectasias, erythema, sebaceous gland hypertrophy and epithelial atypia or dysplasia (Baumann L. *J Pathol*. 2007 January; 211(2):241-51. Skin ageing and its treatment; Han A. Photoaging. Dermatol Clin. 2014: 291-9).

For the most part these changes occur most frequently on areas of chronic exposure including the face, ears, neck, backs of the hands, chest, arms and legs. Buttocks or upper inner arms are often preserved and pristine emphasizing the difference between chronological aging and photoaging.

As the manifestations of photodamage are numerous many options of treatment are proposed, such as: chemical peels, dermabrasion, injectable fillers, botulinum toxin and surgery, as well as topical treatments such as the use of retinoids and lately ablative and non-ablative resurfacing lasers carbon dioxide laser, ND-Yag, Q-switched, KTP and pulsed-dye lasers and intensed pulsed light (IPL)), radiofrequency and photodynamic therapy (PDT) as alternatives. (Shamban A T. Current and new treatments of photodamaged skin. Facial Plast Surg. 2009 December; 25(5):337-46.)

Nowadays photodynamic therapy (PDT), a recognized and approved treatment for nonmelanoma skin cancers and their precursors such as actinic keratosis, as well as for other organ and mucosal epithelial conditions, sees its indications enlarging to inflammatory or infectious conditions (e.g. psoriasis, acne, leishmaniosis). PDT involves the application of a photosensitizing (photochemotherapeutic) agent to the affected area of the body, followed after an incubation period to the exposure to a photoactivating light that will convert the photosensitizing agent into a cytotoxic form, followed by necrosis and apoptosis of the target tissue A range of photosensitizing agents is known, including the psoralens, the porphyrins (e.g. Photofrin (Registered trademark)), the chlorins and the phthalocyanins. Amongst the most clinically useful photosensitizing agents known in the art, however, are 5-aminolevulinic acid and its derivatives, for example esters such as 5-ALA esters. These, through an intra cellular metabolism will be converted by the haem biosynthetic pathway predominantly to protoporhyrin IX (PpIX).

The mechanism of action of PDT relies on intracellular porphyrins (including PpIX) that are photoactive, fluorescing compounds and, upon light activation in the presence of oxygen, singlet oxygen is formed which causes damage to cellular compartments, in particular the mitochondria. Light activation of accumulated porphyrins leads to a photochemical reaction and thereby phototoxicity to the light-exposed target cells.

Although PDT is clinically useful in the treatment of a wide range of diseases, a major drawback of such treatment is the concomitant side-effects, particularly at the treatment site. These often include inflammation such as erythema, swelling, edema, burning, itching, exfoliation, hyperpigmentation and prolonged irritation and hypersensitivity after treatment. Such side-effects are particularly undesirable when the treatment site is the face, scalp or neck.

A need still therefore exists for alternative PDT methods especially using natural daylight with reduced or no undesirable side effects (e.g. inflammation, pain, etc.) as well as lower downtime but which have high therapeutic efficacy.

SUMMARY OF THE INVENTION

The present invention relates to a PDT treatment of photodamaged skin, comprising subjecting the skin of a subject in need thereof to a pre-treatment such as mechanical ones (like dermoabrasion (e.g. with sand paper) or microneeding (e.g. with a dermaroller)) or chemical ones like peeling. The inventors have surprisingly found that such mechanical pre-treatment is as efficient in cosmetically or therapeutically treating photodamaged skin without, or with reduced, adverse effects observed with a pretreatment implemented with ablative fractional laser. The PDT then comprises applying onto said skin a photosensitizer, in particular 5-MAL. In a representative embodiment, the photosensitizer is applied for a duration comprised between 4 minutes to 4 hours, in particular between 15 minutes and 3 hours.

The present inventors have also surprisingly found that application of a photosensitizer for a shorter time period that is classically implemented in a PDT, allows the implementation of a PDT as efficient as in the case where the photosensitizer is used for a longer period of time, with greatly reduced side effects usually observed in the prior art PDT protocols.

Therefore, the invention also relates to a PDT treatment of photodamaged skin, comprising administering to a subject in need thereof a photosensitizer, in particular 5-MAL, for a short duration and then removing the photosensitizer from the skin surface. This PDT protocol is alternatively designated pulse-PDT herein.

Representative photosensitizers include preferably 5-aminolevulinic acid (5-ALA) and derivatives (e.g. an ester) of 5-ALA, more preferably 5-ALA methyl ester (or 5-MAL), or a pharmaceutically acceptable salt thereof. In the present uses and methods, photactivation is achieved by natural or artificial light. In a particular embodiment, the PDT comprises:

(a) optionally, preparing the area of skin to be treated with the appropriate pre-treatment, in particular a mechanical pretreatment such as a curettage, dermoabrasion or micro-needling (or micro perforation),
(b) administering to said animal a composition comprising said photosensitizer, in particular for a short duration; and
(c) photoactivating said photosensitizer.

In a particular embodiment, the invention implements a pulse-PDT treatment, comprising administering to a subject in need thereof a photosensitizer, in particular 5-MAL, for a short duration and then removing the photosensitizer from the skin surface. Photoactivation is then carried out as described throughout the present application. The pulse-PDT treatment of the invention ensures high intracellular PPIX and low extracellular PPIX. Excess amounts of PPIX formation during and after the end of the treatment are thus avoided. In particular, the inventors show that the pulse-PDT treatment of the invention shows less inflammation with unchanged efficacy.

According to an embodiment, the pulse time during which the photosensitizer is let on the skin is comprised between 5 and 120 minutes. According to a preferred embodiment, the pulse time during which the photosensitizer is let on the skin is comprised between 15 and 60 minutes, in particular between 20 and 40 minutes. In a further particular embodiment, the photosensitizer is administered for about 30 minutes (e.g. for 25, 26, 27, 28, 29, 30, 31, 32, 33, 34 or 35 minutes, more particularly during 30 minutes).

DETAILED DESCRIPTION OF THE INVENTION

By the term "animal" is meant herein any human or non-human being. Preferred animals for treatment in accordance with the invention are humans.

In a particular embodiment, the subject is a male or female human subject. In another particular embodiment, the subject is of the Fitzpatrick I, II, III, IV, V or VI skin type. In a further embodiment, the subject is of the I, II or III skin type, more particularly of the II or III skin type.

In another embodiment, the subject's skin Dover's global photodamage score before treatment if of 2, 3 or 4, in particular of 2 or 3.

Photodamage occurs when skin of an organism is exposed to ultraviolet (especially ultraviolet-B, UVB), leading to skin damage. Exposure to UV radiation will accelerate the accumulation of ROS and free radicals in skin cells, increase oxidative stress to the skin cells and induce expression of matrix metalloproteinases (MMP), thereby resulting in oxidative photodamage. Molecular changes of photoaging are reflected by the alteration of keratinocytes, melanocytes fibroblasts and endothelial cells by UV. The morphologic changes are: thickening of epidermis, increased melanocyte density and epidermal melanin, abnormal elastic tissue, increased collagen degradation, thickening of the vascular walls All these changes are translated by clinical signs such as dryness, sallowness, fine and severe wrinkling, irregulat dark/light pigmentation, laxity, elastosis (yellow, cobblestoned effect), telegiectasia, sebaceous gland hyperplasis and in advanced cases, premalignant and malignant lesions care occur. Chronic actinic damage of facial skin. Clin Dermatol. 2014 November-December; 32(6):752-62)

Photosensitizers

Use of 5-ALA (5-amino-4-oxo-pentanoic acid, otherwise known as 5-aminolevulinic acid) and derivatives of 5-ALA in PDT is well known in the scientific and patent literature (see, for example, J. C. Kennedy et al., J. Clin. Laser Med. Surg. (1996) 14: 289-304, U.S. Pat. Nos. 5,079,262, 5,211, 938, 5,234,940, 5,422,093, 6,034,267, WO91/01727, WO96/28412, WO2005/092838 and WO2006/051269). 5-ALA and all such derivatives of 5-ALA, as well as their pharmaceutically acceptable salts, are suitable for the uses and methods herein described.

The 5-ALA derivatives useful in accordance with the invention may be any derivative of 5-ALA capable of forming protoporphyrin IX (PpIX) or any other photosensitizer (e.g. a PpIX derivative) in vivo. Typically, such derivatives will be a precursor of PpIX or of a PpIX derivative (e.g. a PpIX ester) and which are therefore capable of inducing an accumulation of PpIX at the site to be treated following administration in vivo. Suitable precursors of PpIX or PpIX derivatives include 5-ALA prodrugs which might be able to form 5-ALA in vivo as an intermediate in the biosynthesis of PpIX or which may be converted (e.g. enzymatically) to porphyrins without forming 5-ALA as an intermediate. Esters of 5-aminolevulinic acid and N-substituted derivatives thereof are preferred photosensitizers for use in the invention. Those compounds in which the 5-amino group is unsubstituted (i.e. the ALA esters) are particularly preferred. Such compounds are generally known and described in the literature (see, for example, WO96/28412, WO02/10120 and WO2005/092838 to PhotoCure ASA). Esters of 5-aminolevulinic acid with substituted or unsubstituted alkanols, i.e. alkyl esters are especially preferred photosensitizers for use in the invention. In particular, 5-MAL and 5-MAL derivatives are particularly preferred. Examples of useful derivatives include those of general formula I:

$$R^2{}_2N\text{—}CH_2COCH_2\text{—}CH_2CO\text{—}OR^1 \qquad (I)$$

Wherein:

$R^1$ represents a substituted or unsubstituted straight, branched or cyclic alkyl group (e.g. a substituted or unsubstituted straight-chained alkyl group); and each $R^2$ independently represents a hydrogen atom or an optionally substituted alkyl group, e.g. a group $R^1$; and pharmaceutically acceptable salts thereof.

As used herein, the term "alkyl", unless stated otherwise, includes any long or short chain, cyclic, straight-chained or branched aliphatic saturated or unsaturated hydrocarbon group. The unsaturated alkyl groups may be mono- or polyunsaturated and include both alkenyl and alkynyl groups. Unless stated otherwise, such groups may contain up to 40 atoms. However, alkyl groups containing up to 30, preferably up to 10, particularly preferably up to 8, especially preferably up to 6, e.g. up to 4 carbon atoms, for example 1, 2, 3 or 4 carbon atoms, are preferred.

The substituted alkyl $R^1$ and $R^2$ groups may be mono or poly-substituted.

Suitable substituents may be selected from hydroxy, alkoxy, acyloxy, alkoxycarbonyloxy, amino, aryl, nitro, oxo, fluoro, -SR3, —$NR^3{}_2$ and —$PR^3{}_2$ groups, and each alkyl group may be optionally interrupted by one or more —O—, —$NR^3$—, —S— or —$PR^3$— groups, in which $R^3$ is a hydrogen atom or a $C_{1-6}$ alkyl group).

Preferred substituted alkyl $R^1$ groups include those carrying one or more oxo groups, preferably straight-chained $C_{4-12}$ alkyl (e.g. $C_{8-10}$ alkyl) groups substituted by one, two or three (preferably two or three) oxo groups. Examples of such groups include 3,6-dioxa-1-octyl and 3,6,9-trioxa-1-decyl groups.

Particularly preferred for use in the invention are those compounds of formula I in which at least one $R^2$ represents a hydrogen atom. In especially preferred compounds each $R^2$ represents a hydrogen atom.

Compounds of formula I in which $R^1$ represents an unsubstituted alkyl group (preferably $C_{1-8}$ alkyl, e.g. $C_{1-6}$ alkyl) or an alkyl group (e.g. $C_{1-2}$ alkyl, especially $C_1$ alkyl)

substituted by a substituent as hereinbefore defined (e.g. by an aryl group such as phenyl or by an alkoxy group such as methoxy) are also preferred.

Unsubstituted alkyl groups which may be used in the invention include both branched and straight-chained hydrocarbon groups. Compounds of formula I in which $R^1$ is a $C_{4-8}$, preferably a $C_{5-8}$, straight chain alkyl group which is branched by one or more $C_{1-6}$ (e.g. $C_{1-2}$ alkyl) groups are preferred. Representative examples of suitable unsubstituted branched alkyl groups include 2-methylpentyl, 4-methylpentyl, 1-ethylbutyl and 3,3-dimethyl-1-butyl. 4-methylpentyl is particularly preferred.

Compounds of formula I in which $R^1$ is a $C_{1-10}$ straight-chained alkyl group are also preferred. Representative examples of suitable unsubstituted alkyl groups include methyl, ethyl, propyl, butyl, pentyl, hexyl and octyl (e.g. n-propyl, n-butyl, n-pentyl, n-hexyl and n-octyl). Hexyl, especially n-hexyl, is a particularly preferred group. Methyl is also particularly preferred.

Also preferred for use in the invention are those compounds of formula I in which $R^1$ represents a $C_{1-2}$ alkyl group (preferably a $C_1$ alkyl group) optionally substituted by an aryl group.

Still further preferred for use in the invention are those compounds of formula I in which $R^1$ represents an alkyl group (e.g. $C_{1-2}$ alkyl, especially $C_1$ alkyl) substituted by an aryl group (e.g. phenyl). Preferred substituted alkyl $R^1$ groups which may be present in compounds of formula I include $C_{1-6}$ alkyl, preferably $C_{1-4}$ alkyl, particularly preferably $C_1$ or $C_2$ alkyl (e.g. $C_1$ alkyl) substituted (preferably terminally substituted) by an optionally substituted aryl group.

By an "aryl group" is meant a group which is aromatic. Preferred aryl groups comprise up to 20 carbon atoms, more preferably up to 12 carbon atoms, for example, 10 or 6 carbon atoms.

Aryl groups which may be present in the compounds of the invention may be heteroaromatic (e.g. 5-7 membered heteroaromatics) but are preferably nonheteroaromatic. By "non-heteroaromatic" is meant an aryl group having an aromatic system comprising electrons originating solely from carbon atoms. Preferred aryl groups include phenyl and napthyl, especially phenyl. In preferred compounds for use in the invention one or two aryl groups may be present, preferably one.

Aryl groups which may be present in the compounds of the invention may optionally be substituted by one or more (e.g. 1 to 5), more preferably one or two, groups (e.g. one group). Preferably the aryl group is substituted at the meta or para position, most preferably the para position. Suitable substituent groups may include haloalkyl (e.g. trifluoromethyl), alkoxy (i.e. —OR groups wherein R is preferably a $C_{1-6}$ alkyl group), halo (e.g. iodo, bromo, more especially chloro and fluoro), nitro and $C_{1-6}$ alkyl (preferably $C_{1-4}$ alkyl). Preferred $C_{1-6}$ alkyl groups include methyl, isopropyl and t-butyl, particularly methyl. Particularly preferred substituent groups include chloro and nitro. Still more preferably the aryl group is unsubstituted.

In a further preferred aspect the invention provides the use of a photosensitiser which is a compound of formula I wherein $R^1$ represents an aryl substituted $C_{1-4}$ alkyl group (preferably $C_{1-2}$, e.g. $C_1$), preferably wherein said aryl group comprises up to 20 carbon atoms (e.g. up to 12 carbon atoms, especially 6 carbon atoms) and is itself optionally substituted, and each $R^2$ is as hereinbefore described.

Preferred compounds for use in the invention include methyl ALA ester, ethyl ALA ester, propyl ALA ester, butyl ALA ester, pentyl ALA ester, hexyl ALA ester, octyl ALA ester, 2-methoxyethyl ALA ester, 2-methylpentyl ALA ester, 4-methylpentyl ALA ester, 1-ethylbutyl ALA ester, 3,3-dimethyl-1-butyl ALA ester, benzyl ALA ester, 4-isopropyl benzyl ALA ester, 4-methyl benzyl ALA ester, 2-methyl benzyl ALA ester, 3-methylbenzyl ALA ester, 4-[t-butyl] benzyl ALA ester, 4-[trifluoromethyl]benzyl ALA ester, 4-methoxybenzyl ALA ester, 3,4-[dichloro]benzyl ALA ester, 4-chlorobenzyl ALA ester, 4-fluorobenzyl ALA ester, 2-fluorobenzyl ALA ester, 3-fluorobenzyl ALA ester, 2,3,4,5,6-pentafluorobenzyl ALA ester, 3-nitrobenzyl ALA ester, 4-nitrobenzyl ALA ester, 2-phenylethyl ALA ester, 4-phenylbutyl ALA ester, 3-pyridinyl-methyl ALA ester, 4-diphenyl-methyl ALA ester and benzyl-5-[(1-acetyloxyethoxy)-carbonyl]amino levulinate.

Still further preferred compounds for use in the invention include methyl ALA ester, ethyl ALA ester, 2-methoxyethyl ALA ester, benzyl ALA ester, 4-isopropylbenzyl ALA ester, 4-methylbenzyl ALA ester, 2-methylbenzyl ALA ester, 3-methylbenzyl ALA ester, 4[t-butyl]benzyl ALA ester, 4-[trifluoromethyl]benzyl ALA ester, 4-methoxybenzyl ALA ester, 3,4[di-chloro]benzyl ALA ester, 4-chlorobenzyl ALA ester, 4-fluorobenzyl ALA ester, 2-fluorobenzyl ALA ester, 3-fluorobenzyl ALA ester, 4-nitrobenzyl ALA ester, 2-phenylethyl ALA ester, 4-phenylbutyl ALA ester, 3-pyridinyl-methyl ALA ester, 4-diphenyl-methyl ALA ester and benzyl-5-[(l-acetyloxyethoxy)-carbonyl]amino levulinate.

Particularly preferred compounds for use in the invention include methyl ALA ester, hexyl ALA ester and benzyl ALA ester, especially methyl ALA ester.

The compounds for use in the invention may be prepared by any conventional procedure available in the art (e.g. as described in WO02/10120 to PhotoCure ASA). For example, esters of 5-ALA may be prepared by reaction of 5-ALA with the appropriate alcohol in the presence of acid. Alternatively compounds for use in the invention may be available commercially (e.g. from Photocure ASA, Norway).

Other photosensitizers that can be used in the field of the present invention can be 1,1' bis (2 ethyl 1,3 dioxolan 2 yl) cryptocyanine, 3 carbethoxypsoralen, 4,4',6 trimethylangelicin, 4' aminomethyl 4,5',8 trimethylpsoralen, 4' hydroxymethyl 4,5',8 trimethylpsoralen, 5 methylangelicin, aminolevulinic acid hexyl ester, aminolevulinic acid methyl ester, amotosalen, angelicin, bacteriochlorin, benzoporphyrin derivative, bergapten, chloroaluminum phthalocyanine, etiopurpurin, fimaporfin, gadolinium texaphyrin, hematoporphyrin derivative, hypocrellin A, hypocrellin B, lemuteporfin, lutetium texaphyrin, merocyanine, methoxsalen, motexafin, musk ambrette, padeliporfin, padoporfin, photofrin, photofrin I, photofrin II, phthalocyanine, phthalocyanine aluminum, phthalocyanine derivative, phthalocyanine zinc, psoralen, psoralen derivative, rostaporfin, talaporfin, temoporfin, tetrakis (3 hydroxyphenyl) chlorin, tetrakis (4 sulfophenyl) porphine, tetraphenylporphyrin, tetraphenylporphyrin derivative, tetrasulfophthalocyanine, tetrasulfophthalocyanine aluminum, tetrasulfophthalocyanine chloroaluminum, trimethylpsoralen, trioxysalen, verdin derivative, verteporfin.

Photoactivation

According to the present invention, photoactivation is achieved by either an artificial or natural light source. In a preferred embodiment, photoactivation of the photosensitizer is achieve by LED or sunlight.

Penetrations Enhancers or Pre-Treatment

Skin penetration enhancers as well as skin pre-treatment for enhancing penetration of drugs and chemicals have been developed to improve bioavailability. One action among others of these enhancers or pre-treatment procedures is to decrease the skin barrier resistance. These enhancing penetration procedures can be classified as mechanical, physical and chemical pre-treatments.

The table below is a non-limitative list of such pre-treatment/penetration enhancers that may be used according to the invention.

| Mechanical | Physical | Chemical |
|---|---|---|
| Skin preparation pad (sandpaper) Microdermabration microneedling | Ablative (carbon dioxide) and non-ablative lasers (fractional non ablative carbon dioxide, erbiumdoped yttrium aluminium garnet (Er:YAG), IPL) | Superficial peelings (alfa-hydroxy acids, trichloracetic acid, Jessner solution) |
| Curettage tape- stripping pan- scrubber exfoliating scrub compress rubbing | | Retinoids (tretinoin, adapalene, tazarotene) Acid azelaic Vitamin D3 derivates |

Light Sources—Artificial

Electroluminescence (EL) is an optical and electrical phenomenon in which a material emits light in response to the passage of an electric current or to a strong electric field. This is distinct from black body light emission resulting from heat (incandescence), from a chemical reaction (chemiluminescence), sound (sonoluminescence), or other mechanical action (mechanoluminescence).

Among the electroluminescence sources, LED (Light emitting diodes) lamps are well known and preferred as artificial light source in the present invention. A LED lamp (LED light bulb) is a solid-state lamp that uses light-emitting diodes (LEDs) as the source of light. The LEDs involved may be conventional semiconductor light-emitting diodes, organic LEDs (OLED), or polymer light-emitting diodes (PLED) devices.

The LED lamps used in the examples hereafter are defined by some characteristics like wavelength (in nm), power of the LED (irradiance in mW/cm$^2$) energy of the LED (in J/cm$^2$). Such particular features are provided below.

Light Sources—Natural

This aspect of the invention includes photoactivation with either natural sunlight or any light source which provides artificial sunlight (i.e. the entire range from UV to IR). Use of natural sunlight as the light source has the advantage that the animal being treated is free to leave the clinical environment where treatment is normally conducted.

Light Sources—Intensity

In the uses and methods of the invention, photoactivation may be achieved using light sources known in the art. Methods for the irradiation of different areas of the body, e.g. by lamps or lasers are well known in the art (see for example Van den Bergh, Chemistry in Britain, May 1986 p. 430-439). The wavelength of light used for irradiation may be selected to achieve a more efficacious photosensitizing effect. The most effective light is light in the wavelength range 300-800 nm, typically within the 400-700 nm range.

Irradiation with an artificial light is preferably performed for 1 to 30 minutes, preferably for 1 to 15 minutes, more preferably from 5 to 10 minutes, preferably for 5 minutes, depending on the light dose and fluence rate. A single irradiation may be used or alternatively a light split dose in which the light dose is delivered in a number of fractions, e.g. a 1 to 10 minutes between irradiations, may be used.

Photoactivation with natural light is preferably done for a duration between 5 minutes and 4 hours, in particular for a duration of 2 hours. In a particular embodiment, a sunscreen is applied to the sun-exposed area including the treatment area in both groups during natural daylight-PDT, to avoid sunburn.

Treatment of the Skin According to the Invention

The methods and uses of the invention may involve pretreatment of the skin. As the stratum corneum acts as a barrier that limits the penetration of substances through the skin, the purpose of a pretreatment (enhancer) is to favor the absorption of the photosensitizer to the target tissue and thus a higher efficacy. Enhancers may comprise mechanical, physical or chemical preparation of the skin e.g. microdermabrasion (particularly with an adapted skin preparation pad, sandpaper), microneedling, tape-stripping, pan-scrubber, exfoliating scrub, compress rubbing, non ablative lasers at a low-energy delivery and chemical procedures such as superficial peelings (Retinoids (tretinoin, adapalene, tazarotene), Acid azelaic, Vitamin D3 derivates). For example, the pretreatment may comprise a mechanical pretreatment of the skin. Representative mechanical treatments include curettage, dermoabrasion (in particular with an adapted sandpaper or micro-needling (or micro-perforation) before application of the photosensitizer. In a particular embodiment, the pretreatment includes perforation of the skin using an adapted device such as a micro-needle device, for example a dermaroller.

The skin rejuvenating effects of PDT using an artificial light source for photodamaged skin have been documented in several clinical trials. (Jang J I D 2013, Szeimies B J D 2012, Sakamoto B J D 2011, Choi J Y. J Dermatol Science. 2010, Orringer Arch Dermatol 2008, Issa Dermatol Surg 2010, Zane. Laser Surg Med 2007, Bagazgoita B J D 2011). It was raised the issue that PDT with artificial light sources for photorejuvenation can be a painful procedure and therefore often requires specific pain management.

Daylight mediated PDT appears as the ideal procedure addressing to all signs of epidermal and dermal actinic damage with lack of discomfort, lack of pain during therapy, possibility to treat large areas (as demonstrated by several trials showing the same efficacy level of both procedures, using daylight or an artificial source for clearing actinic keratosis with significantly lower pain score, leading to fewer related adverse (Wiegell JEADV 2011).

The use of an enhancer, such as a skin pretreatment as described above, in particular a mechanical pretreatment, more particularly the use of dermabrasion or microneedling, and more particularly using a sandpaper, associating natural light could provide better effects in photodamaged skin with lower side effects.

The methods and uses of the invention may also be carried out with or without occlusion, more preferably with occlusion.

The photosensitizer may be applied for a duration of between 5 minutes to 4 hours, in particular between 15 minutes to 3 hours, in particular between 30 minutes and 2 hours. In a particular embodiment, the photosensitizer may be applied as a pulse therapy for the time periods provided above, for example for a duration of about 30 minutes. The inventors herein show that such a pulse therapy has the advantage of being as efficient as therapy with longer exposures, but with less PPIX produced, thereby preventing side effects associated with PPIX.

In a particular embodiment, the treatment comprises:
(a) optionally, preparing the area of skin to be treated with the appropriate pre-treatment, for example a curettage, a dermoabration or microneedling (micro perforation), in particular a perforation with an adapted microneedling device such as a dermaroller;
(b) administering to said animal a composition comprising said photosensitizer, in particular for a short period of time;
(c) photoactivating said photosensitizer; and
(d) optionally, removing the photosensitizer.

In an embodiment of the invention, the natural daylight photodynamic therapy (PDT) on an animal comprises:
a) optionally, preparing the area of skin to be treated with the appropriate pre-treatment, for example a curettage, a dermoabration or microneedling (micro perforation), in particular a perforation with an adapted microneedling device such as a dermaroller;
b) administering to said animal a composition comprising said photosensitizer for a duration between 5 min to 240 minutes;
c) photoactivating said photosensitizer for a duration between 1 to 15 minutes with artificial light or 0.5 hour to 3 hours with natural light; and
d) Optionally, removing the photosensitizer.

In a more preferred embodiment of the invention the use of a photosensitizer in natural daylight photodynamic therapy (PDT) on an animal comprises:
a) optionally, preparing the area of skin to be treated with the appropriate pre-treatment, for example a curettage, a dermoabration or microneedling (micro perforation), in particular a perforation with an adapted microneedling device such as a dermaroller;
b) administering to said animal a composition comprising said photosensitizer for a duration between 15 min to 180 minutes;
c) photoactivating said photosensitizer for a duration between 0.5 hour to 2 hours with natural light; and
d) optionally, removing the photosensitizer.

In a more preferred embodiment of the invention the photosensitizer for use in photodynamic therapy (PDT) on an animal comprises
a) optionally, preparing the area of skin to be treated with the appropriate pre-treatment, for example a dermoabration (sand-paper) or microneedling (micro perforation), in particular a dermoabration with an adapted sand-paper device such as silicone carbide sand paper;
b) administering to said animal a composition comprising said photosensitizer for a duration of 30 minutes; and
c) photoactivating said for a duration of at least 2 hours with natural light; and
d) optionally, removing the photosensitizer.

Any of the above particular or preferred embodiments may comprise a step of mechanically pretreating the skin as described above, before the step of applying the photosensitizer on the skin.

In a particular embodiment of the invention, PDT of photodamaged skin is applied to treat any one or all of the manifestation of photodamage of the skin: texture (tactile roughness), sallowness (pale skin), wrinkles (fine lines), mottled pigmentation, dyspigmentation (hypo-/hyperpigmentation including solar lentigines), facial erythema and elastosis, with a special interest in fine wrinkles and pigmentary troubles. (including advanced aging or wrinkling, uneven or "pebbly" skin, irregular pigmentation, small blood vessels or red markings (telangiectasias), freckles (ephilides), "liver spots" and "age spots" (lentigines), thinned or fragile skin). In addition, in another embodiment, the PDT of photodamaged skin according to the invention is applied on areas of chronic exposure including the face, ears, neck, backs of the hands, chest, arms and/or legs.

According to another aspect, the invention relates to a kit comprising a device for implementing a pretreatment as provided above, and a composition comprising a photosensitizer as described above. This kit is useful for the implementation of the methods and uses of the present invention. In a particular embodiment, the kit comprises an adapted sandpaper and a composition comprising ALA or esters of ALA such as the methyl ALA ester, hexyl ALA ester and benzyl ALA ester, especially methyl ALA ester. In addition, the kit according to the invention may comprise a sunscreen. The kit of the invention may further comprises instructions to follow for implementing the methods and uses of the invention.

EXAMPLES

Figure 1:
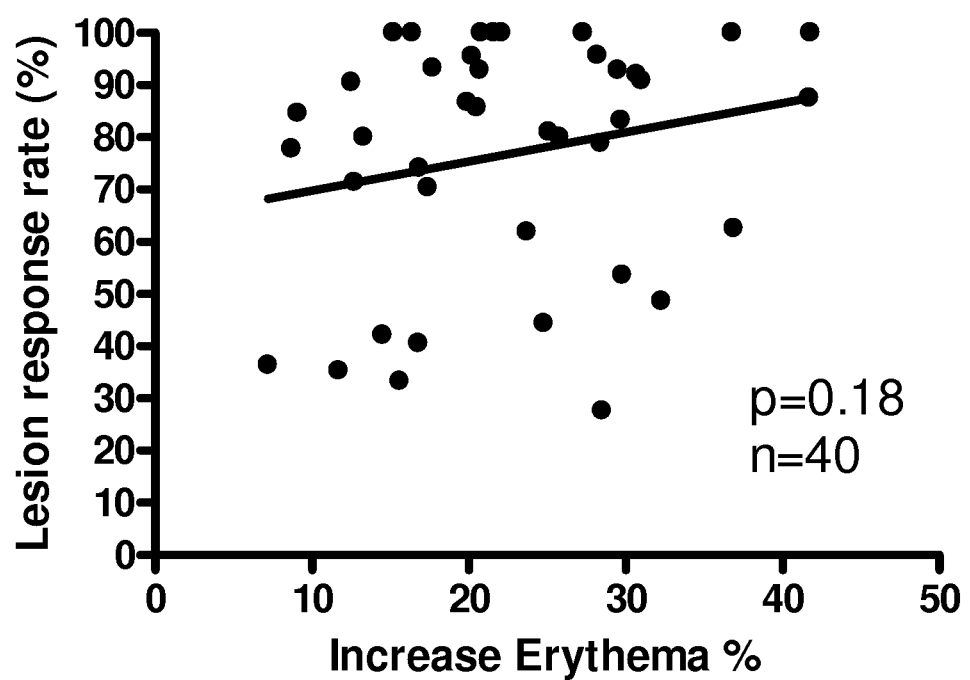
FIG. 1 is a graph showing the inflammation vs. response rate (3 months) of AK on the face.
Figure 2:
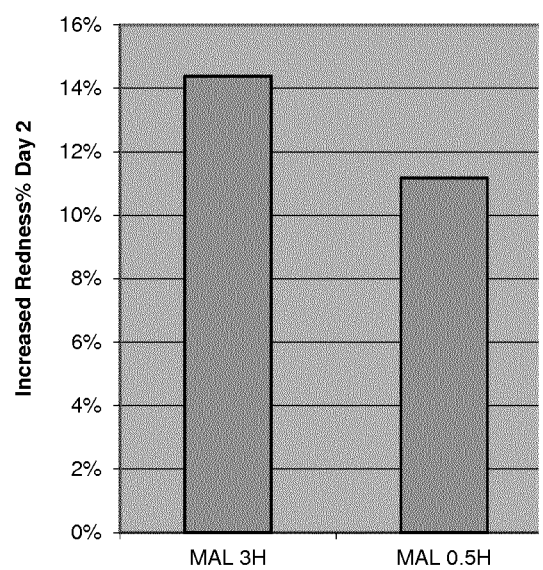
FIG. 2 is a graph showing the mean increased redness the day after PDT.
Figure 3:
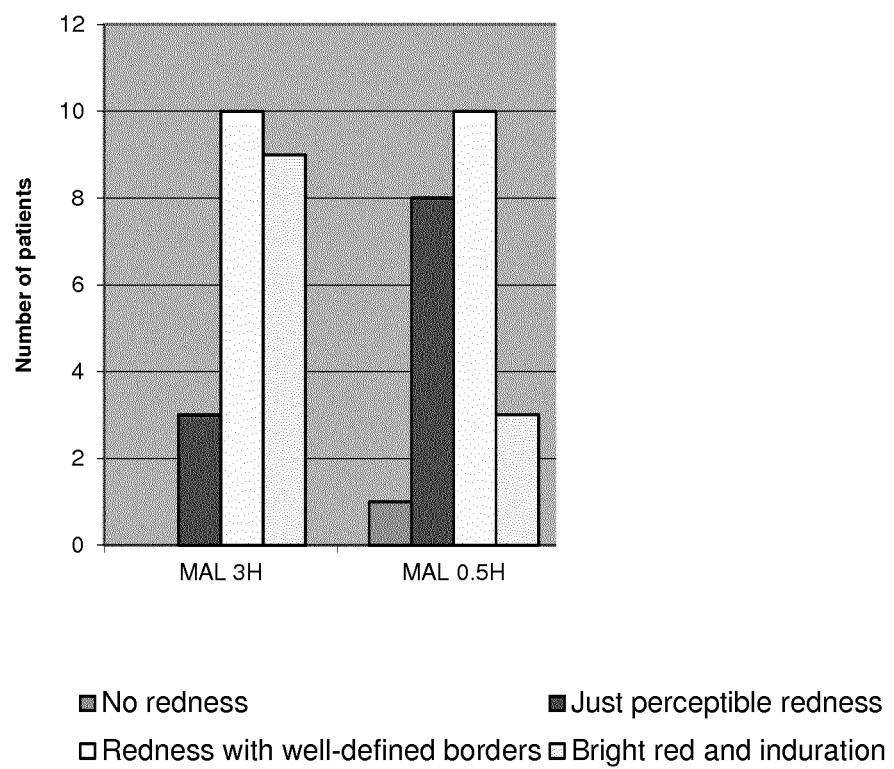
FIG. 3 is a graph reporting the visual redness 1 day after PDT with different treatment protocols.
Figure 4:
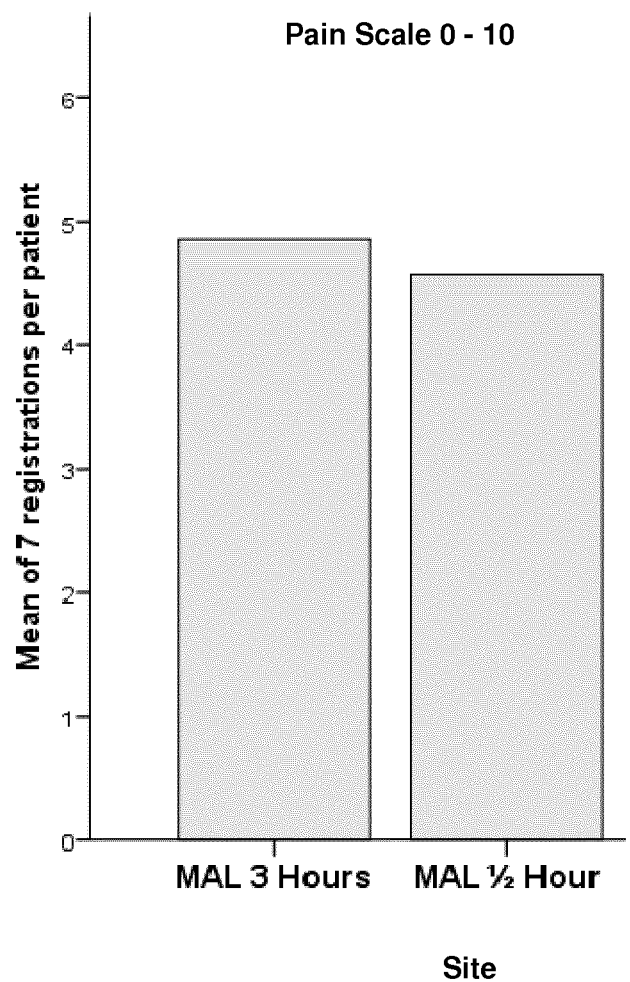
FIG. 4 is a graph showing the pain scale after different treatments.

Example 1—Assessment of the Efficacy of a Daylight PDT in Subjects with Facial Photodamage A double-blind randomized-controlled trial has been conducted to determine whether daylight PDT is an efficient method for treating photodamaged skin.

60 Subjects were randomized to receive 1 gram of topical methyl aminolevulinate (MAL) applied to the whole face <30 minutes before sun exposure for 2 hours (3 sessions, 2 to 4 weeks apart) or matching placebo applied to the whole face <30 minutes before sun exposure for 2 hours (3 sessions, 2 to 4 weeks apart) in a double-blind fashion. Neither the investigator nor the patient knew which agent was administered, as it was applied by a trained professional nurse. To enhance product/placebo penetration a subtle abrasion with sandpaper of the whole face was performed. Also, a sunscreen (Cetaphil Dermacontrol SPF30®) was applied to the entire sun-exposed area including the treatment area in both groups during daylight-PDT, to avoid sunburn.

Efficacy was evaluated after 1 month of the third (last) daylight session.

PDT treatment with MAL followed by daylight exposure was found to have a significantly greater treatment effect than placebo followed by daylight exposure; with the majority of patients of the MAL group having facial improvement (14 out of 30 subjects) and 11 out of 30 having facial success (p=0.00, Chi$^2$ test).

Significant differences were also found in specific photodamage variables:

| Specific photodamage severity scores | Metvix | Placebo | p value |
|---|---|---|---|
| Fine lines | | | |
| failure | 6 (20%) | 27 (90%) | 0.000 |
| improvement | 13 (43.3%) | 2 (6.7%) | |
| sucess | 11 (36.7%) | 1 (3.3%) | |
| Mottled pigmentation | | | |
| failure | 7 (23.3%) | 23 (76.7%) | 0.000 |
| improvement | 18 (60%) | 4 (13.3%) | |
| sucess | 5 (16.7%) | 3 (10%) | |
| Sallowness | | | |
| failure | 5 (16.7%) | 25 (83.3%) | 0.000 |
| improvement | 9 (30%) | 2 (6.7%) | |
| sucess | 16 (53.3%) | 3 (10%) | |
| Tactile roughness | | | |
| failure | 5 (16.7%) | 25 (83.3%) | 0.000 |
| improvement | 6 (20%) | 2 (6.7%) | |
| sucess | 19 (63.3%) | 3 (10%) | |
| Coarse lines | | | |
| failure | 9 (30%) | 27 (90%) | 0.000 |
| improvement | 15 (50%) | 3 (10%) | |
| sucess | 6 (20%) | 0 (0%) | |
| Erythema | | | |
| failure | 6 (20%) | 25 (83.3%) | 0.000 |
| improvement | 16 (53.3%) | 2 (6.7%) | |
| sucess | 8 (26.7%) | 3 (10%) | |

Pain VAS scores after session 1, 2 and 3 were not significantly different between the two groups, although a little bit more pain was experimented by patients in the placebo group after the second session (below table).

Similarly, there were no statistical differences in the effects experimented by patients by patients one week after sessions, and in some of these variables no effect was found depending on each session (below table).

| Other secondary Outcomes | Metvix (Mean (Median)) | Placebo (Mean (Median)) | P |
|---|---|---|---|
| Pain VAS score after session 1 | 0.80 (0) | 0.40 (0) | >0.05 |
| Pain VAS score after session 2 | 0.60 (0) | 1.27 (0) | >0.05 |
| Pain VAS score after session 3 | 1.13 (0) | 0.77 (0) | >0.05 |
| | n(%) | n(%) | |
| Reaction 1 week after session 1 | | | |
| Oozing | | | |
| 0 | 30 (100%) | 30 (100%) | * |
| 1 | 0 (0%) | 0 (0%) | |
| 2 | 0 (0%) | 0 (0%) | |
| 3 | 0 (0%) | 0 (0%) | |
| Erythema | | | |
| 0 | 20 (66.7%) | 25 (83.3%) | >0.05 |
| 1 | 8 (26.7%) | 5 (16.7%) | |
| 2 | 2 (6.7%) | 0 (0%) | |
| 3 | 0 (0%) | 0 (0%) | |
| Oedema | | | |
| 0 | 30 (100%) | 30 (100%) | * |
| 1 | 0 (0%) | 0 (0%) | |
| 2 | 0 (0%) | 0 (0%) | |
| 3 | 0 (0%) | 0 (0%) | |
| Desquamation | | | |
| 0 | 16 (53.3%) | 23 (76.7%) | >0.05 |
| 1 | 9 (30%) | 5 (16.7%) | |
| 2 | 5 (16.7%) | 2 (6.7%) | |
| 3 | 0 (0%) | 0 (0%) | |
| Pigmentation | | | |
| 0 | 29 (96.7) | 29 (96.7%) | >0.05 |
| 1 | 1 (3.3%) | 1 (3.3%) | |
| 2 | 0 (0%) | 0 (0%) | |
| 3 | 0 (0%) | 0 (0%) | |
| Vesiculation | | | |
| 0 | 30 (100%) | 30 (100%) | * |
| 1 | 0 (0%) | 0 (0%) | |

-continued

| | | | |
|---|---|---|---|
| 2 | 0 (0%) | 0 (0%) | |
| 3 | 0 (0%) | 0 (0%) | |
| Reaction 1 week after session 2 | | | |
| Oozing | | | |
| 0 | 30 (100%) | 30 (100%) | * |
| 1 | 0 (0%) | 0 (0%) | |
| 2 | 0 (0%) | 0 (0%) | |
| 3 | 0 (0%) | 0 (0%) | |
| Erythema | | | |
| 0 | 19 (63.3%) | 22 (73.3%) | >0.05 |
| 1 | 11 (36.7%) | 8 (26.7%) | |
| 2 | 0 (0%) | 0 (0%) | |
| 3 | 0 (0%) | 0 (0%) | |
| Oedema | | | |
| 0 | 30 (100%) | 30 (100%) | * |
| 1 | 0 (0%) | 0 (0%) | |
| 2 | 0 (0%) | 0 (0%) | |
| 3 | 0 (0%) | 0 (0%) | |
| Desquamation | | | |
| 0 | 15 (50%) | 23 (76.7%) | >0.05 |
| 1 | 12 (40%) | 7 (23.3%) | |
| 2 | 3 (10%) | 0 (0%) | |
| 3 | 0 (0%) | 0 (0%) | |
| Pigmentation | | | |
| 0 | 29 (96.7%) | 30 (100%) | >0.05 |
| 1 | 1 (3.3%) | 0 (0%) | |
| 2 | 0 (0%) | 0 (0%) | |
| 3 | 0 (0%) | 0 (0%) | |
| Vesiculation | | | |
| 0 | 30 (100%) | 30 (100%) | * |
| 1 | 0 (0%) | 0 (0%) | |
| 2 | 0 (0%) | 0 (0%) | |
| 3 | 0 (0%) | 0 (0%) | |
| Reaction 1 week after session 3 | | | |
| Oozing | | | |
| 0 | 30 (100%) | 30 (100%) | * |
| 1 | 0 (0%) | 0 (0%) | |
| 2 | 0 (0%) | 0 (0%) | |
| 3 | 0 (0%) | 0 (0%) | |
| Erythema | | | |
| 0 | 23 (76.7%) | 26 (86.7%) | >0.05 |
| 1 | 7 (23.3%) | 4 (13.3%) | |
| 2 | 0 (0%) | 0 (0%) | |
| 3 | 0 (0%) | 0 (0%) | |
| Oedema | | | |
| 0 | 30 (100%) | 30 (100%) | * |
| 1 | 0 (0%) | 0 (0%) | |
| 2 | 0 (0%) | 0 (0%) | |
| 3 | 0 (0%) | 0 (0%) | |
| Desquamation | | | |
| 0 | 15 (50%) | 22 (73.3%) | >0.05 |
| 1 | 12 (40%) | 8 (26.7%) | |
| 2 | 3 (10%) | 0 (0%) | |
| 3 | 0 (0%) | 0 (0%) | |
| Pigmentation | | | |
| 0 | 26 (86.7%) | 28 (93.3%) | >0.05 |
| 1 | 4 (13.3%) | 2 (6.7%) | |
| 2 | 3 (10%) | 0 (0%) | |
| 3 | 0 (0%) | 0 (0%) | |
| Vesiculation | | | |
| 0 | 30 (100%) | 30 (100%) | * |
| 1 | 0 (0%) | 0 (0%) | |
| 2 | 0 (0%) | 0 (0%) | |
| 3 | 0 (0%) | 0 (0%) | |

Example 2—Comparison of Mechanical Penetration Enhancers on Photosensitizer Skin Penetration The effect on the product skin penetration of different mechanical penetration enhancement techniques (occlusion, microneedles, ablative fractional laser) has been evaluated.

10 healthy volunteers have been treated according to the following protocol:
pretreatment with either micro-needles (Dermaroller) or ablative fractional laser ($CO_2$ laser fraxel repair (SOLTA)), or no pretreatment;
application of Metvix;
3 hours of incubation with or without occlusion.
Penetration was quantified during incubation using measurement of photo fluorescence of PpIX at 30 minutes, 1 hour, 2 hours, and 3 hours after product application.

Figure 10:
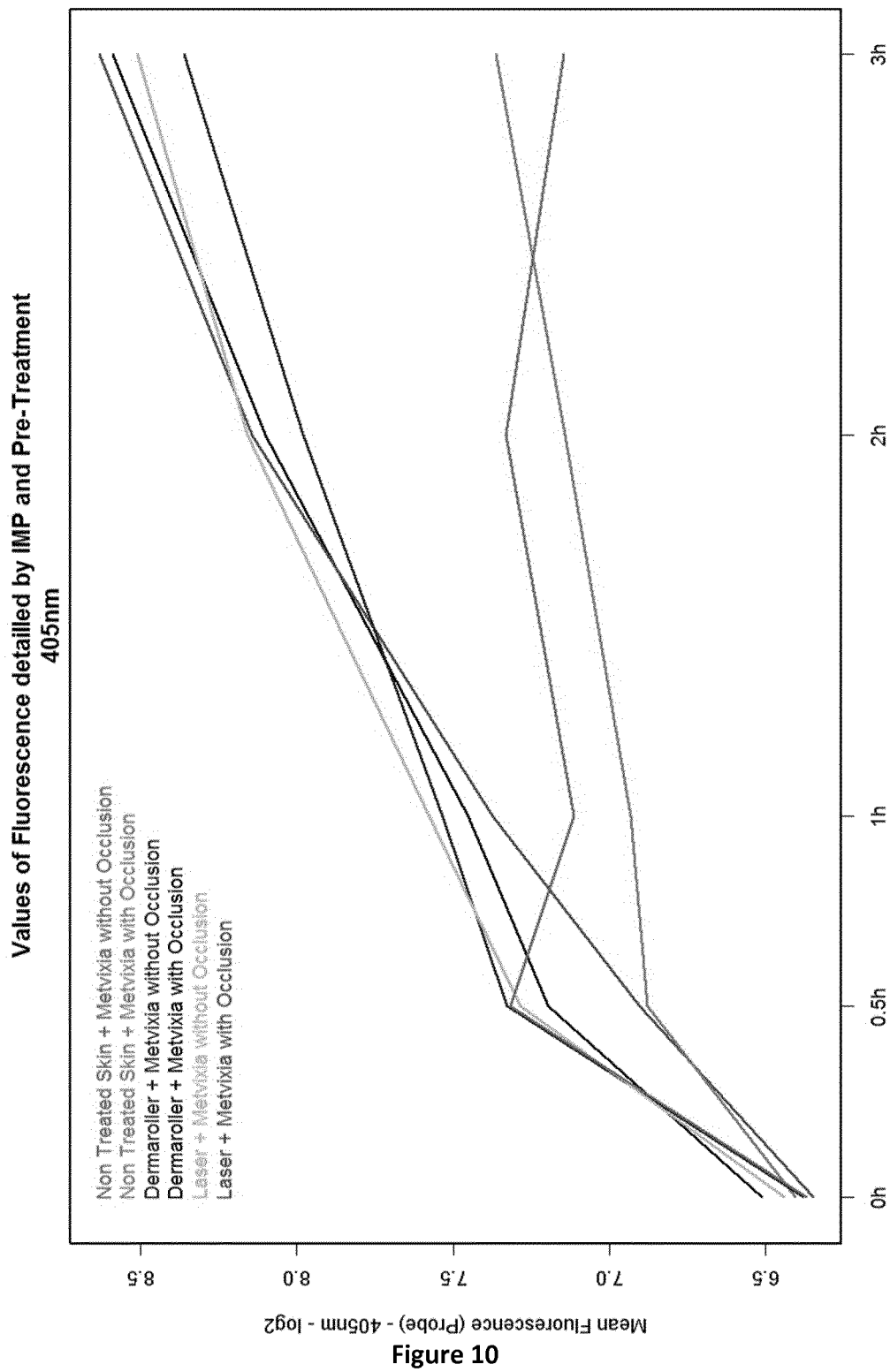
FIG. 10 is a graph showing the values of fluorescence by IMP and pre-treatment at 405 nm
Figure 11:
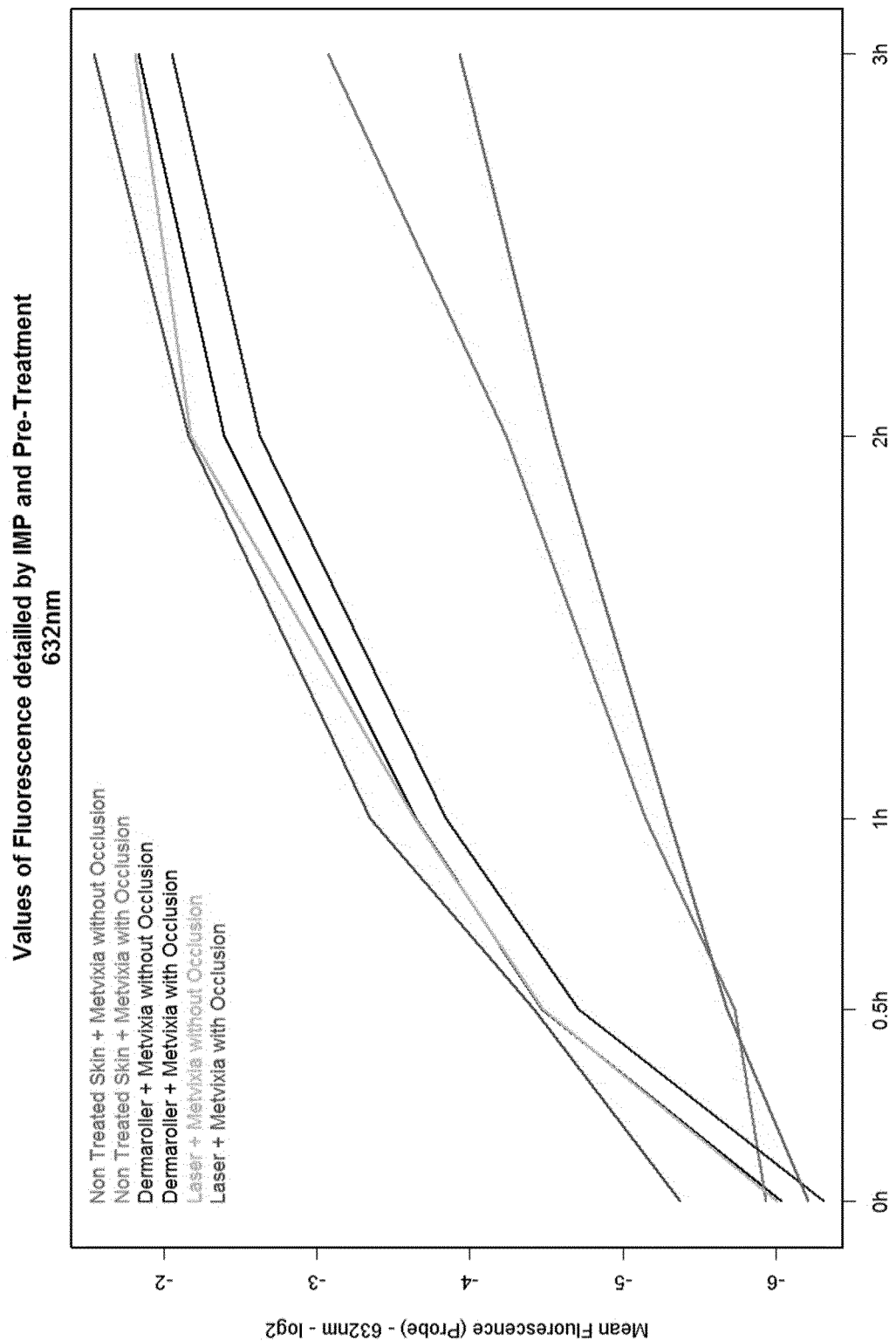
FIG. 11 is a graph showing the values of fluorescence by IMP and pre-treatment at 632 nm

Both Dermaroller and laser similarly increased Metvix penetration in surface and deeper skin as measured by blue (405 nm) (see FIG. 10) and red (632 nm) (see FIG. 11) photo fluorescence as compared to no pretreatment without occlusion and no pretreatment with occlusion.

No difference was observed with or with occlusion before 3 hours.

Figure 12:
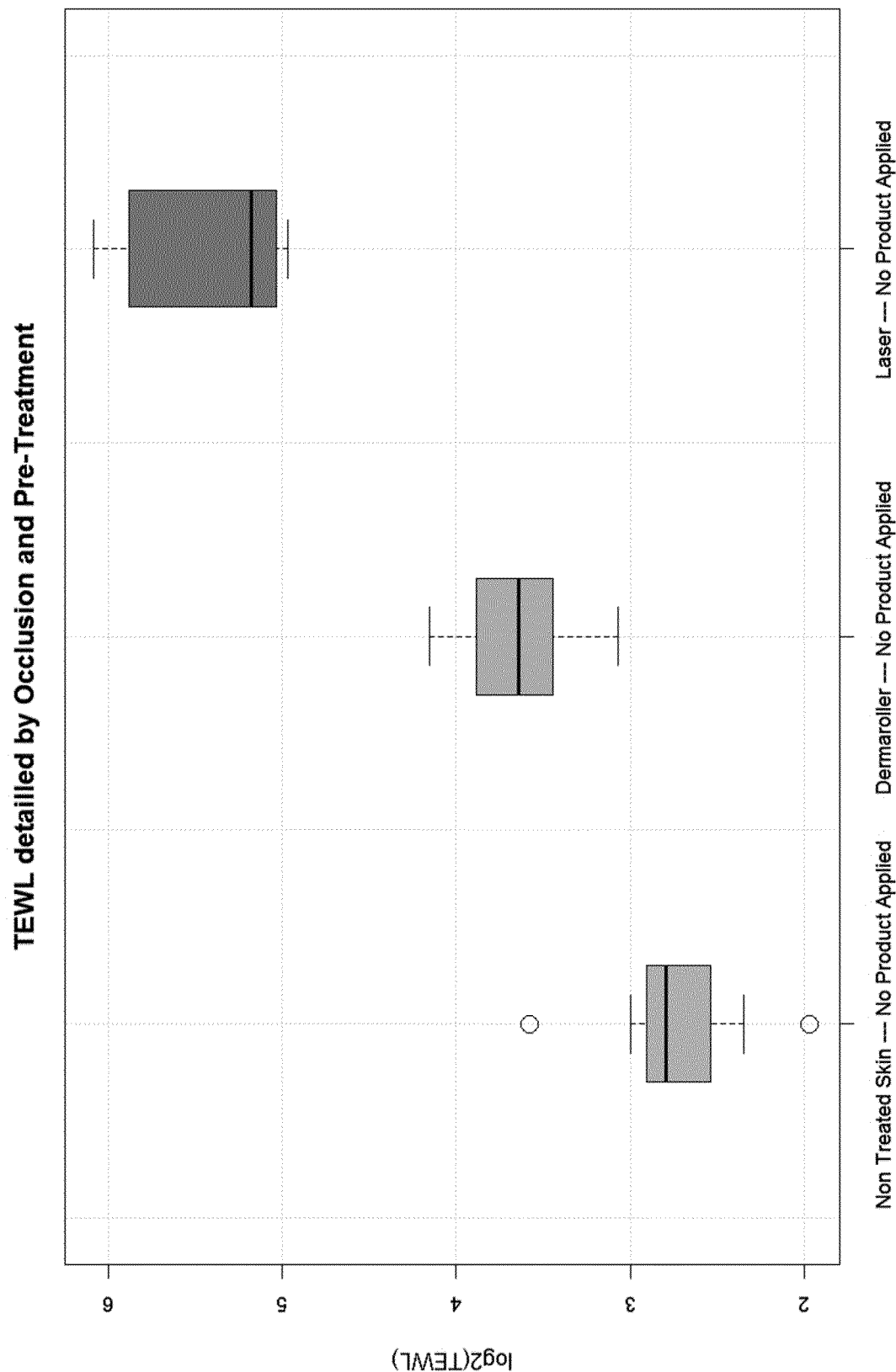
FIG. 12 is a graph showing TEWL detailed by occlusion and pre-treatment

In addition, laser pretreatment was found to be more painful and more irritant than Dermaroller, and laser pretreatment has more impact in lowering skin barrier function as observed by measuring transepidermal water loss, (see FIG. 12)

Therefore, the inventors have surprisingly shown that mechanical pretreatment with a device such as micro-needle device is as efficient as a laser pretreatment to increase product skin penetration but with less adverse events and is therefore more adapted to the PDT treatment of photodamaged skin.

Example 3—PDT Procedure Change to Minimize Inflammation in PDT

According to the just mentioned theory it would be preferable to keep PPIX and cellular enzymes away from the extracellular compartment, thereby avoiding inflammation.

The purpose of this project is therefore to keep the PPIX formation within the mitochondria and avoid excess amounts of PPIX to be formed. Simultaneously PPIX should be allowed to be formed for such a long time that most unnormal cells will be affected.

So the purpose of PDT is to kill unnormal cells, preferably by apoptosis. The ideal situation would be to keep PPIX inside the cell and to destroy the mitochondria only, thereby inhibiting the ATP formation necessary for cell functions. That should result in cell death by apoptosis.

One possible way to achieve this would be to give a short 5-MAL pulse treatment to get a high concentration of 5-MAL in the cells initially and then diminish further access to 5-MAL by removing 5-MAL from the skin surface.

This could be done by only exposing the skin to 5-MAL for a short time, after which all 5-MAL is removed from the skin surface. If the right "pulse time" can be found it might ensure high cellular PPIX and low extracellular PPIX. Excess amounts of PPIX formation during and after the end of the treatment would thus be avoided.

The result shows less inflammation with unchanged efficacy and thus mitochondria destruction seems to be the most important factor in PDT.

Figure 5:
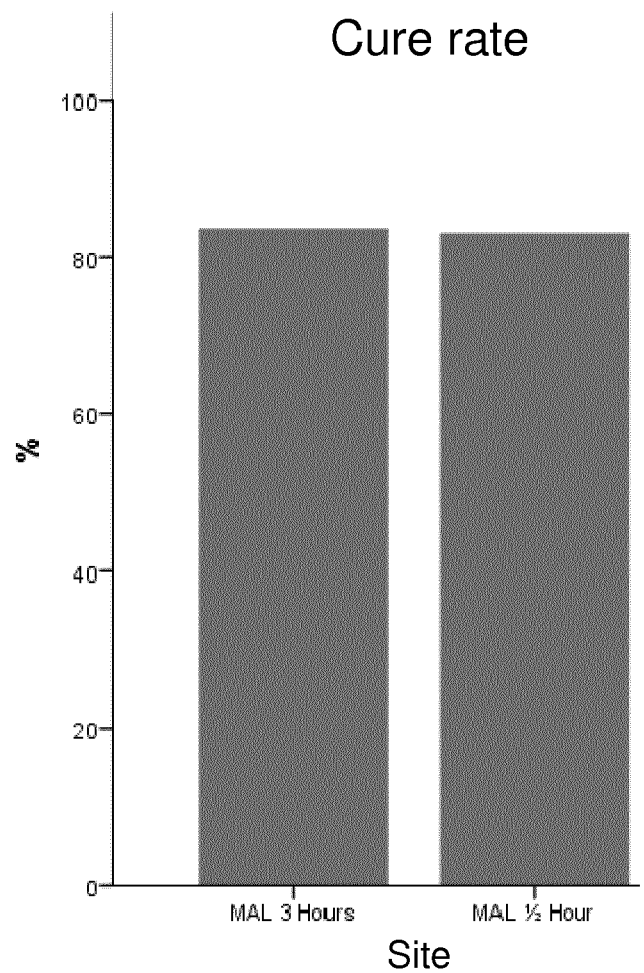
FIG. 5 is a graph showing the cure rate after different treatments.
Figure 6:
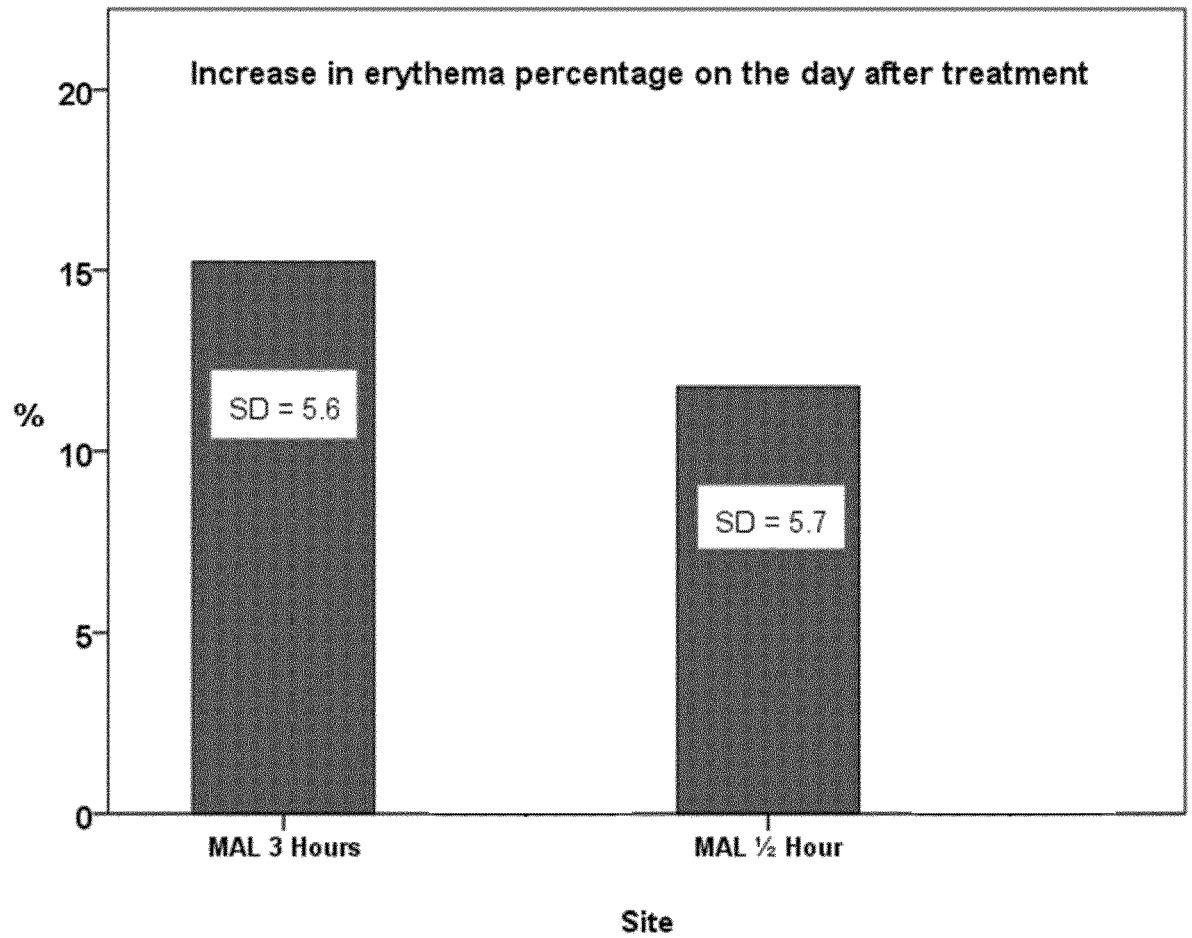
FIG. 6 is a graph showing the increase in erythema percentage one day after treatment with different protocols.
Figure 7:
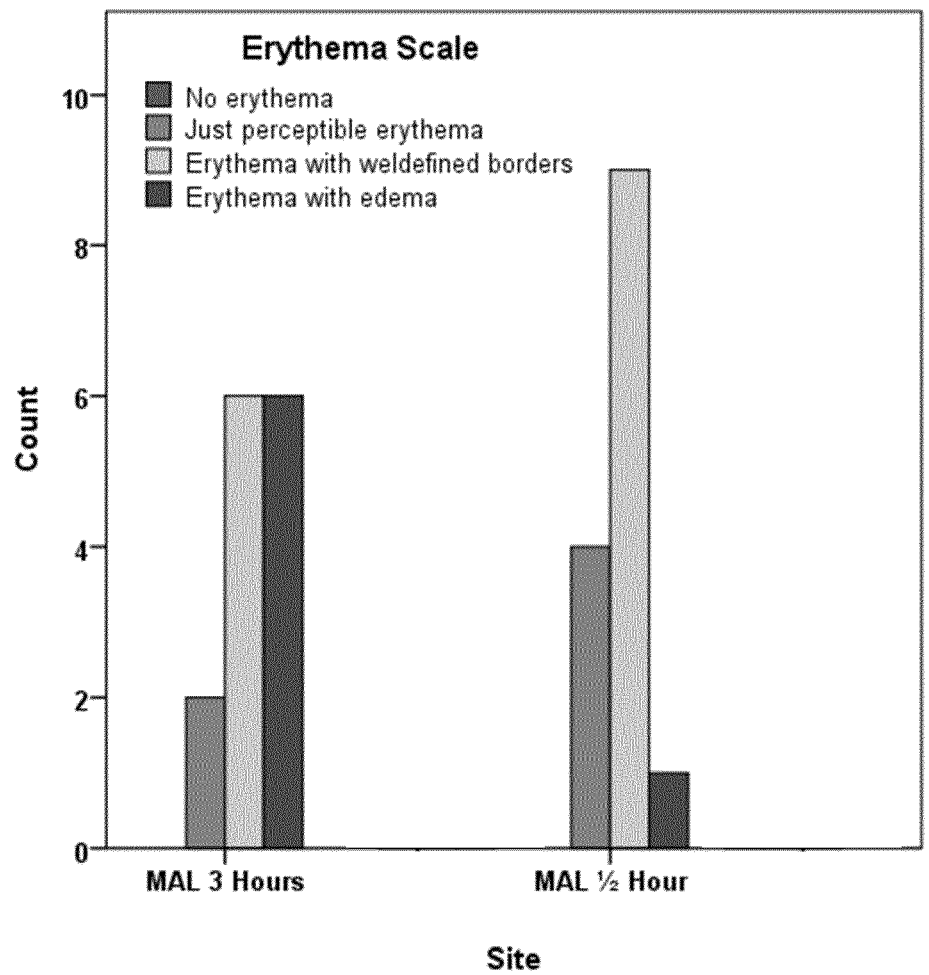
FIG. 7 is a graph showing erythema scale after treatment with different protocols.
Figure 8:
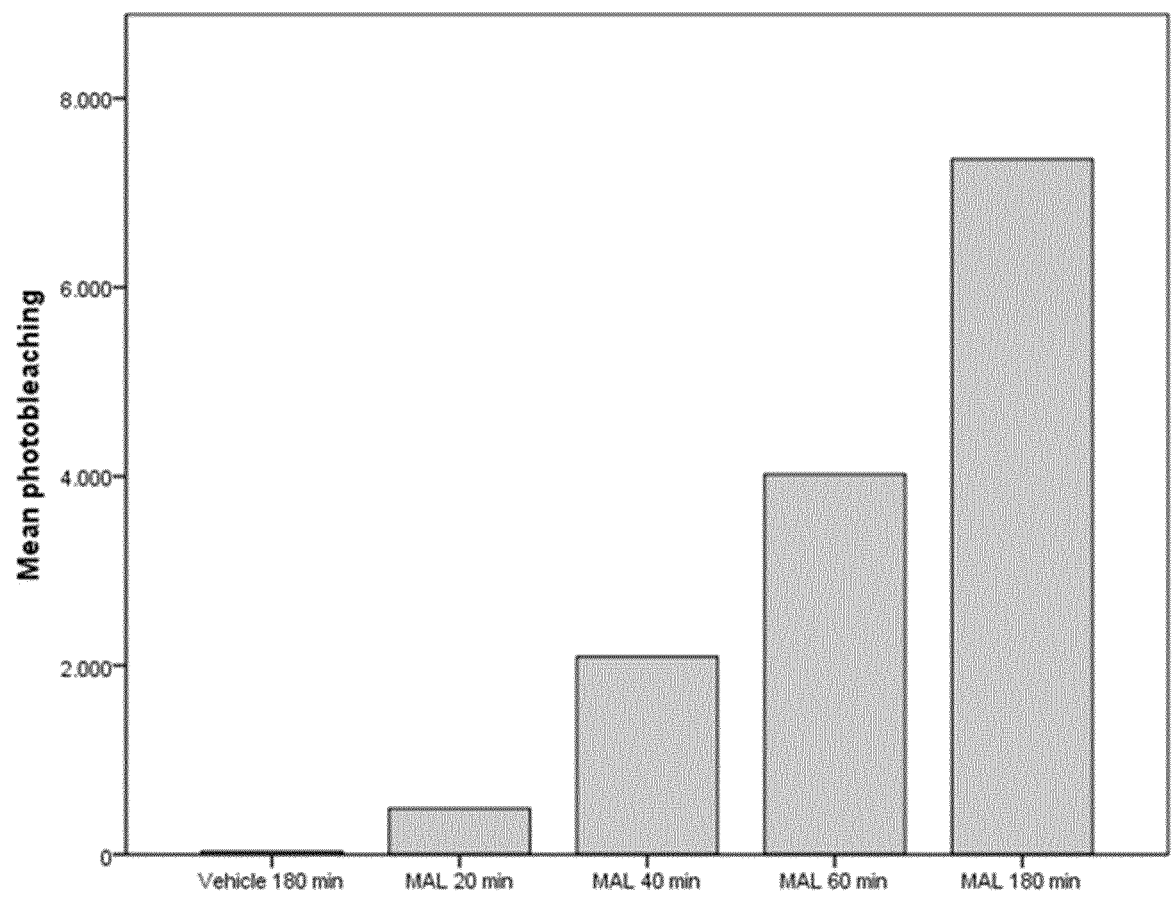
FIG. 8 is a graph showing the mean photobleaching in the standard treatment and a different "pulse" treatment.
Figure 9:
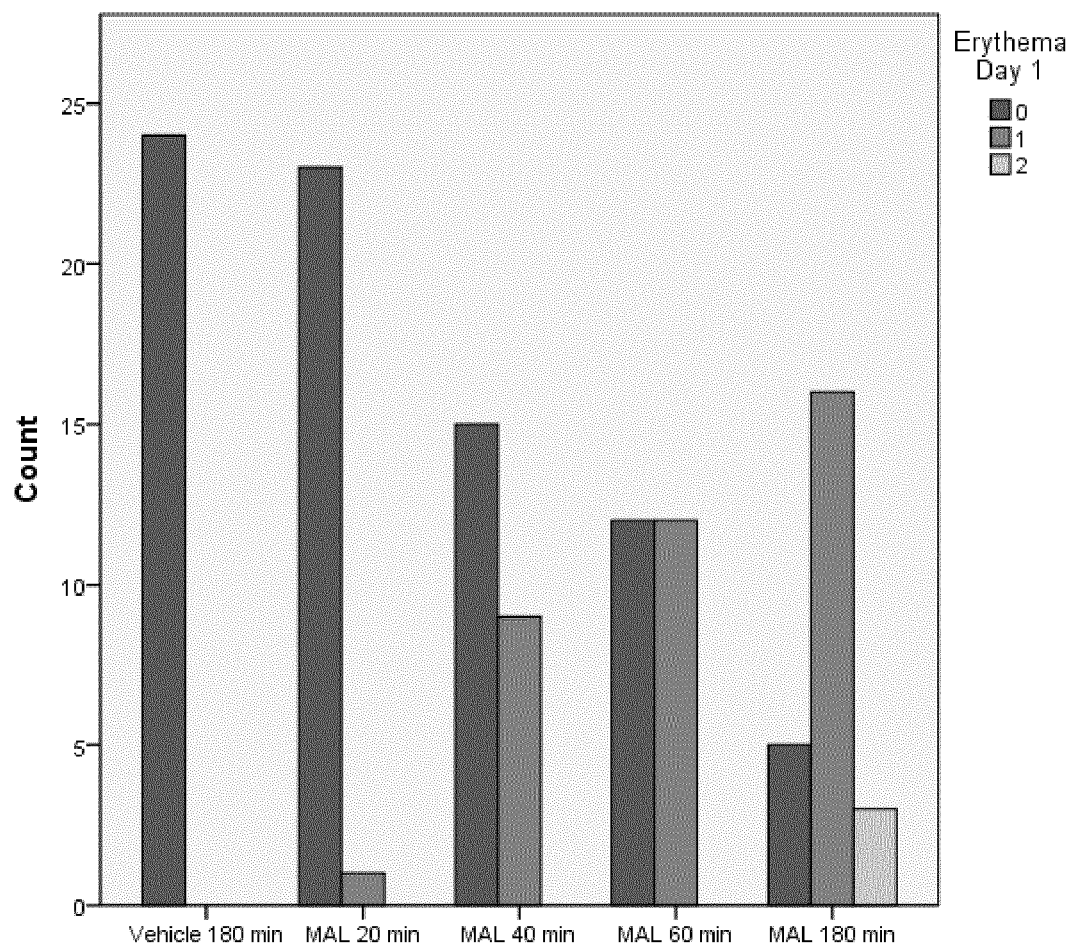
FIG. 9 is a graph showing the inflammation (erythema)/PpIX formation relationship.

To estimate the preferable Metvix "pulse time" a separate investigation was performed (Method B) on 24 healthy volunteers. The pulse time was 20 min., 40 min., 60 min., and the conventional 180 min, after which excess amounts of Metvix was removed from the skin. The formation of PPIX after 3 hours is seen in FIG. 8, and the relation to inflammation is seen in FIG. 9. It is seen that PPIX concentration speeds up between 20-40 min. of "pulse exposure", and so we have chosen 30 min. as the minimum "pulse exposure" time in the following (Method A) investigation of efficacy and inflammation by this method change. The results are illustrated in Column 3 in FIGS. 4, 5, 6, and 7. The procedure change clearly diminishes inflammation (erythema), without affecting the cure rate (FIG. 5). Pain level is not changed. PPIX concentration is clearly lower than for the conventional 3-hour exposure to Metvix (Table 1 and FIG. 8).

Methods

Healthy Volunteers

Twenty-four healthy male volunteers of Scandinavian ancestry were included in the study (mean age years, range 20-51). A treatment area was selected on the inside of both forearms of the volunteer. Each treatment area was divided into four minor treatment fields of the size 2×5 cm with at least 3 cm between each field using a prefabricated flexible template. In order to imitate skin lesions all fields were tape stripped 10 times with occlusive dressing before treatment (Tegaderm™ Roll, 3M, Glostrup, Denmark).

On the left forearm vehicle Unguentum M was applied to the treatment field.

On the right forearm excess amounts of 5-MAL 16% (Metvix®, Photocure, Oslo, Norway) were applied to all four fields of treatment. All fields were covered with light-impermeable, occlusive dressing. After 20 minutes the dressing was removed from the first field and the excess cream gently wiped off. The field was covered again with a thin piece of gauze and light impermeable dressing. After additional 20 and 40 min same procedure was followed with the second and third field. 180 min after application of 5-MAL and vehicle was removed from all five fields, and the excess cream was gently wiped of the last field. All fields were illuminated with red light. Illumination was performed with red LED light 630 nm peak (Aktilite™ 128; Photocure ASA, Oslo Norway) using a total light dose of 37 $J/cm^2$ given over 9 min. During and after illumination pain was recorded. The volunteers were equipped with a special diary for recording pain in the days after treatment. Four follow-up visits were performed at day 1, 2, 3 and 8 after treatment.

PpIX Fluorescence

5-MAL-induced PpIX fluorescence was depicted non-invasively using a fluorescence camera (Medeikonos AB, Gothenburg, Sweden). The amount of PpIX fluorescence was calculated from the photographs by the program MatLab® (MatLab®, MathWorks, Natic, US). The amount of fluorescence was measured before tape stripping and cream application (baseline) and before and after illumination.

The photo bleaching is then the difference in PpIX fluorescence (AU) calculated from the pre and post illumination images.

Erythema and Pigmentation

As an indicator of inflammation erythema was measured. The erythema was assessed by an expert evaluator and measured objectively.

The objective measurements of erythema and pigmentation were performed using a skin reflectance meter (Optimize Scientific 558, Chromo-Light, Espergaerde, Denmark).

Erythema % and pigmentation % were measured before treatment, immediately before illumination, immediately after illumination, and at the four follow-up visits.

Pain Score

The volunteers scored their pain every minute during illumination, and recorded their pain in the diary every hour after illumination on the treatment day, twice per day the next three days and once a day on the following five days. Since PDT was performed at different times of the day the number of evaluations differed from 3 to 11 the first day. Pain was assessed using a numerical scale ranging from 0 to 10, where 0 is no pain and 10 is worst imaginable pain. To make it easier for the patients to identify the different treated fields, the dairy was supplied with numbered drawings of the fields.

Randomizing

The study was designed as an open randomised trial. A statistical adviser made the randomisation. Since the sequence of treatment duration was predefined, randomization was only determining which of the four treatment fields should be the first.

Statistics

The sample size was calculated on the bases of data from the literature. We set the minimal clinical relevant difference to 8.8% (50% of the earlier found 17.6%) and choose a power of 0.80 and a significance level of 0.05, 22 volunteers should be included.

To identify differences in pain score, erythema % and pigmentation % between the treatment fields we used Wilcoxon Signed Ranked Test, since all results were paired.

For all calculations a p-value <0.05 was considered statistical significant. All analyses were performed with PASW Statistics 19.0 for Windows (SPSS Inc, Chicago, Ill., USA).

The invention claimed is:

1. A method of treating photodamaged skin of an animal, the method comprising:
   (a) subjecting the photodamaged skin of the animal to mechanical pretreatment comprising dermabrasion, microneedling, and/or sandpaper;
   (b) administering to the photodamaged skin a composition comprising a photosensitizer for 20 minutes to 40 minutes;
   (c) removing the photosensitizer; and
   (d) exposing the photodamaged skin to natural light for 0.5 hour to 3 hours;
   wherein the photosensitizer is selected from the group consisting of 5-aminolevulinic acid (5-ALA) or derivatives thereof represented by general formula I:

$$R^2{}_2N\text{---}CH_2COCH_2\text{---}CH_2CO\text{---}OR^1 \quad (I)$$

wherein:
$R^1$ represents a substituted or unsubstituted straight, branched or cyclic alkyl group; and each $R^2$ independently represents a hydrogen atom or an optionally substituted alkyl group; and pharmaceutically acceptable salts thereof.

2. The method according to claim 1, wherein the photosensitizer represented by general formula I is a methyl ester of 5-aminolevulinic acid (5-methyl ALA ester).

3. The method according to claim 1, wherein the photosensitizer is 5-ALA or 5-methyl ALA ester.

4. The method according to claim 1, wherein the administration of the photosensitizer is carried out without occlusion.

5. The method according to claim 1, wherein the mechanical pretreatment is selected from the group consisting of dermabrasion and microneedling.

6. The method according to claim 1, wherein the natural light source is sunlight.

7. The method according to claim 1, wherein the mechanical pretreatment is with sandpaper.

8. The method according to claim 1, wherein the administering of the composition occurs for a duration selected from the group consisting of 27, 28, 29, 30, 31, and 32 minutes.

9. The method according to claim 8, wherein the duration is 30 minutes.

10. The method according to claim 1, wherein $R^1$ is a substituted or unsubstituted straight-chained alkyl group.

11. The method according to claim 1, wherein the administration is carried out with occlusion.

* * * * *